United States Patent
Avisar et al.

(10) Patent No.: US 12,340,479 B2
(45) Date of Patent: Jun. 24, 2025

(54) SYSTEM AND METHOD FOR AUTOMATIC TRANSFER FUNCTION

(71) Applicant: Surgical Theater, Inc., Los Angeles, CA (US)

(72) Inventors: Mordechai Avisar, Highland Heights, OH (US); Alon Yakob Geri, Orange Village, OH (US); Yuval Faust, Binyamina (IL); Sukhpal Singh, New York, NY (US)

(73) Assignee: Surgical Theater, Inc., Beachwood, OH (US)

( * ) Notice: Subject to any disclaimer, the term of this patent is extended or adjusted under 35 U.S.C. 154(b) by 212 days.

(21) Appl. No.: 17/548,560

(22) Filed: Dec. 12, 2021

(65) Prior Publication Data

US 2022/0207844 A1 Jun. 30, 2022

Related U.S. Application Data

(60) Provisional application No. 63/125,936, filed on Dec. 15, 2020.

(51) Int. Cl.
| | |
|---|---|
| *G06T 19/20* | (2011.01) |
| *G06T 7/00* | (2017.01) |
| *G06T 17/00* | (2006.01) |
| *G06V 10/50* | (2022.01) |
| *G06V 30/40* | (2022.01) |
| *G16H 30/40* | (2018.01) |

(52) U.S. Cl.
CPC ............ *G06T 19/20* (2013.01); *G06T 7/0012* (2013.01); *G06T 17/00* (2013.01); *G06V 10/50* (2022.01); *G16H 30/40* (2018.01); *G06T 2207/30004* (2013.01); *G06T 2219/2012* (2013.01); *G06V 2201/03* (2022.01)

(58) Field of Classification Search
CPC ..................... G06T 17/00; G06T 19/20; G06T 2207/30004; G06T 2219/2012; G06T 7/0012; G06V 10/50; G06V 2201/03; G16H 30/40
See application file for complete search history.

(56) References Cited

U.S. PATENT DOCUMENTS

| | | | |
|---|---|---|---|
| 5,793,888 A * | 8/1998 | Delanoy ................. | G06F 18/40 707/E17.023 |
| 2009/0136130 A1* | 5/2009 | Piper ...................... | G06F 16/00 382/170 |

(Continued)

*Primary Examiner* — Sing-Wai Wu (57) ABSTRACT

A system and method comprising a computer system and database configured using artificial intelligence software for storing historical histograms derived from images of particular biological features of different patients. The stored histograms are each associated with a transfer function that can be used in a 3D model of the biological features to allow users of the model to better observe particular features of the model. The system will automatically determine a transfer function for a new scan(s) by deriving a current histogram of the new scan, comparing this current histogram with the historical histograms stored in the database, and selecting the histogram that is closest to the current histogram based on certain features. The transfer function associated with the closest histogram is then used to obtain a new transfer function for the current histogram for use in a 3D model of the new scan(s).

26 Claims, 8 Drawing Sheets

(56) References Cited

U.S. PATENT DOCUMENTS

| | | | |
|---|---|---|---|
| 2013/0148883 A1* | 6/2013 | Lee | G06F 16/785 |
| | | | 382/165 |
| 2014/0126798 A1* | 5/2014 | Hundley | G01R 33/283 |
| | | | 382/131 |
| 2017/0035517 A1* | 2/2017 | Geri | A61B 90/37 |

* cited by examiner

SYSTEM AND METHOD FOR AUTOMATIC TRANSFER FUNCTION

CROSS-REFERENCES TO RELATED APPLICATIONS

This application claims the benefit of U.S. provisional patent application Ser. No. 63/125,936, filed on Dec. 15, 2020 and incorporated herein by reference.

BACKGROUND

Conventional approaches for providing 3D models of various subjects, such as biological tissues or mechanical components, often require the transformation of visual information to make the models more meaningful to a viewer. Modifying displayed images by changing the brightness, transparency, coloring, contrast, or other features of different components can allow the user to better see individual components, and even to better see behind, through, or around components. But such transformations may utilize transfer functions that are dependent on the initial images from which the model is being build, necessitating customized transfer functions to work appropriately.

Alternatively, utilizing existing transfer functions for images that are similar visually would be a time saver, although manually searching images and their associated transfer functions would be time consuming. An automated means of selecting existing transfer functions from related images would be useful in saving time and effort.

SUMMARY

Provided are a plurality of example embodiments, including, but not limited to, a method for using a computer system to automatically determine a transfer function for use with a 3D model, comprising the steps of:
  storing a plurality of histograms in a database, each one of said histograms derived from one or more associated medical scans of a particular anatomical feature of a respective one of a plurality of different patients;
  storing a plurality of transfer functions in the database, each one of said transfer functions being associated with a respective one of said plurality of histograms;
  generating a current histogram from a specific medical scan of the particular anatomical feature of a particular patient using the computer system;
  the computer system automatically comparing the current histogram to each one of said plurality of histograms to determine if one of said plurality of histograms is sufficiently similar to the current histogram;
  if it was determined that one of said plurality of histograms is sufficiently similar to the current histogram, select the transfer function associated with the one of said plurality of histograms for preparing a model of the particular anatomical feature; and
  if it was determined that none of said plurality of histograms was sufficiently similar to the current histogram, generate a new transfer function for preparing a 3D model of the particular anatomical feature.

Also provided is a method for using a computer system to automatically determine a transfer function for use with a 3D model, comprising the steps of:
  storing a plurality of histograms in a database, each one of said histograms derived from one or more associated image scans of a particular feature of a respective one of a plurality of different subjects;
  storing a plurality of transfer functions in the database, each one of said transfer functions being associated with a respective one of said plurality of histograms;
  generating a current histogram from an image scan of the particular feature of a particular subject using the computer system;
  for each one of the plurality of histograms, the computer system automatically comparing the current histogram to the one of said plurality of histograms to assign a score indicating similarity between the current histogram and the one of the histograms;
  determine whether the score having the highest value is above a threshold value to indicate that the current histogram is sufficiently similar to the one of the plurality of histograms associated with said score with the highest value;
  if it was determined that one of said plurality of histograms associated with the highest score is sufficiently similar to the current histogram, select the transfer function associated with the one of said plurality of histograms associated with the highest score for preparing a 3D model of the particular feature;
  if it was determined that none of said plurality of histograms was sufficiently similar to the current histogram, generate a new transfer function for preparing a 3D model of the particular feature;
  adding the current histogram to the plurality of histograms stored in the database; and
  adding the new transfer function to the plurality of transfer functions stored in the database, said new transfer function being associated with the current histogram.

Still further provided is a method for using a computer system to automatically determine a transfer function for use with a 3D model, comprising the steps of:
  storing a plurality of histograms in a database, each one of said histograms derived from one or more associated medical scans of a particular biological feature of a respective one of a plurality of different patients;
  storing a plurality of transfer functions in the database, each one of said transfer functions being associated with a respective one of said plurality of histograms;
  generating a current histogram from an image scan of the particular biological feature of a particular patient using the computer system;
  for each one of the plurality of histograms, the computer system automatically comparing the current histogram to the one of said plurality of histograms to assign a score indicating similarity between the current histogram and the one of the histograms;
  determine whether the score having the highest value is above a threshold value to indicate that the current histogram is sufficiently similar to the one of the plurality of histograms associated with said score with the highest value;
  if it was determined that one of said plurality of histograms associated with the highest score is sufficiently similar to the current histogram, select the transfer function associated with the one of said plurality of histograms associated with the highest score for preparing a 3D biological model of the particular biological feature;
  if it was determined that none of said plurality of histograms was sufficiently similar to the current histogram, generate a new transfer function for preparing a 3D biological model of the particular feature;

adding the current histogram to the plurality of histograms stored in the database; and adding the new transfer function to the plurality of transfer functions stored in the database, said new transfer function being associated with the current histogram.

Also provided is a method for using a computer system to automatically determine a transfer function for use with a 3D model, comprising the steps of:

storing a plurality of histograms in a database, each one of said histograms capturing voxel intensity values from one or more associated medical scans of a particular biological feature of a respective one of a plurality of different patients;

storing a plurality of transfer functions in the database, each one of said transfer functions being associated with a respective one of said plurality of histograms and being configured to map the voxel intensity values to color and opacity;

generating a current histogram from an image scan of the particular biological feature of a particular patient using the computer system;

for each one of the plurality of histograms, the computer system automatically comparing the current histogram to the one of said plurality of histograms to assign a score indicating similarity between the current histogram and the one of the histograms;

determine whether the score having the highest value is above a threshold value to indicate that the current histogram is sufficiently similar to the one of the plurality of histograms associated with said score with the highest value;

if it was determined that one of said plurality of histograms associated with the highest score is sufficiently similar to the current histogram, select the transfer function associated with the one of said plurality of histograms associated with the highest score for preparing a 3D biological model of the particular biological feature;

if it was determined that none of said plurality of histograms was sufficiently similar to the current histogram, generate a new transfer function for preparing a 3D biological model of the particular feature;

adding the current histogram to the plurality of histograms stored in the database; and adding the new transfer function to the plurality of transfer functions stored in the database, said new transfer function being associated with the current histogram, wherein the 3D biological model, using the selected or new transfer function, provides the ability to control tissue intensity of the particular anatomical feature to enable a user to see features that would otherwise not be seen when using a model.

Still further provided is a system comprising the computer and database for performing any of the above methods.

Also provided are additional example embodiments, some, but not all of which, are described hereinbelow in more detail.

BRIEF DESCRIPTION OF THE DRAWINGS

In the accompanying drawings, structures are illustrated that, together with the detailed description provided below, describe exemplary embodiments of the claimed invention. Like elements are identified with the same reference numerals. It should be understood that elements shown as a single component may be replaced with multiple components, and elements shown as multiple components may be replaced with a single component. The drawings are not to scale and the proportion of certain elements may be exaggerated for the purpose of illustration.

DETAILED DESCRIPTION

The following acronyms and definitions will aid in understanding the detailed description:

VR—Virtual Reality—A 3Dimensional computer generated environment which can be explored and interacted with by a person in varying degrees.

HMD—Head Mounted Display refers to a headset which can be used in VR environments. It may be wired or wireless. It may also include one or more add-ons such as headphones, microphone, HD camera, infrared camera, hand trackers, positional trackers etc.

SNAP Model—A SNAP case refers to a 3D texture or 3D objects created using one or more scans of a patient (CT, MR, fMR, DTI, etc.) in DICOM file format. It also includes different presets of segmentation for filtering specific ranges and coloring others in the 3D texture. It may also include 3D objects placed in the scene including 3D shapes to mark specific points or anatomy of interest, 3D Labels, 3D Measurement markers, 3D Arrows for guidance, and 3D surgical tools. Surgical tools and devices have been modeled for education and patient specific rehearsal, particularly for appropriately sizing aneurysm clips.

MD6DM—Multi Dimension full spherical virtual reality, 6 Degrees of Freedom Model. It provides a graphical simulation environment which enables the physician to experience, plan, perform, and navigate the intervention in full spherical virtual reality environment.

Fly-Through—Also referred to as a tour, this describes a perspective view of a virtual reality environment while moving through the virtual reality environment along a defined path.

A surgery rehearsal and preparation tool previously described in U.S. Pat. No. 8,311,791 and U.S. Patent Publication No. 2019/0080515, incorporated in this application by reference, has been developed to convert static CT and MRI medical images into dynamic and interactive multi-dimensional full spherical virtual reality, six (6) degrees of freedom models ("MD6DM") based on a prebuilt SNAP model that can be used by physicians to simulate medical procedures in real time. The MD6DM provides a graphical simulation environment which enables the physician to experience, plan, perform, and navigate the intervention in full spherical virtual reality environment. In particular, the MD6DM gives the surgeon the capability to navigate using a unique multidimensional model, built from traditional two-dimensional patient medical scans, that gives spherical virtual reality 6 degrees of freedom (i.e. linear; x, y, z, and angular, yaw, pitch, roll) in the entire volumetric spherical virtual reality model.

The MD6DM is rendered in real time by an image generator using a SNAP model built from the patient's own data set of medical images including CT, MM, DTI etc., and is patient specific. A representative brain model, such as Atlas data, can be integrated to create a partially patient specific model if the surgeon so desires. The model gives a 360° spherical view from any point on the MD6DM. Using the MD6DM, the viewer is positioned virtually inside the anatomy and can look and observe both anatomical and pathological structures as if he were standing inside the patient's body. The viewer can look up, down, over the shoulders etc., and will see native structures in relation to each other, exactly as they are found in the patient. Spatial relationships between internal structures are preserved and can be appreciated using the MD6DM.

The algorithm of the MD6DM rendered by the image generator takes the medical image information and builds it into a spherical model, a complete continuous real time model that can be viewed from any angle while "flying" inside the anatomical structure. In particular, after the CT, MRI, etc. takes a real organism and deconstructs it into hundreds of thin slices built from thousands of points, the MD6DM reverts it to a 3D model by representing a 360° view of each of those points from both the inside and outside.

The SNAP model has the ability to display "Tissue specific intensity." Dataset slices are collected and stacked to reconstruct a cube of pixels, also referred to as the voxels cube. The 3D model is a cube volume of voxels. A transfer function is used to map each voxel intensity value to color and opacity and translate it to our viewer's point of view in our 360 model. In this way the tissue intensity is controlled, enabling a surgeon to see what he typically can't see. This innovative feature allows surgeons to see behind arteries and other critical structures and only display relevant anatomy of interest.

Creating a transfer function, however, can be time consuming and costly to create. It may be a manual process done by an individual for each model being created, and therefore takes substantial resources to accomplish, and hence the resulting transfer functions and their outputs may lack consistency and vary in form from time to time depending on the skill and capability of the individual generating the transfer function. As a result, the resulting 3D models utilizing the unique transfer functions may also lack consistency and vary in form from time to time. Moreover, multiple transfer functions may be required in order to highlight different features in a model, further increasing costs and inconsistencies across the models.

Described herein is a system and method for obtaining transfer functions automatically for use in new model development, based on historical information. In particular, the system automates the process of providing a transfer function for a new model by using histograms of the scanned images to compare images to each other to allow automation, thereby eliminating, or at least reducing, the need for manual input. This allows a new category of customers to access and use the surgery rehearsal and preparation tool previously described to create and customize SNAP models in instances where extensive manual labor may not be available. Automating the process of obtaining an appropriate transfer function also allows for better scaling of a surgery rehearsal and preparation tool.

Figure 1:
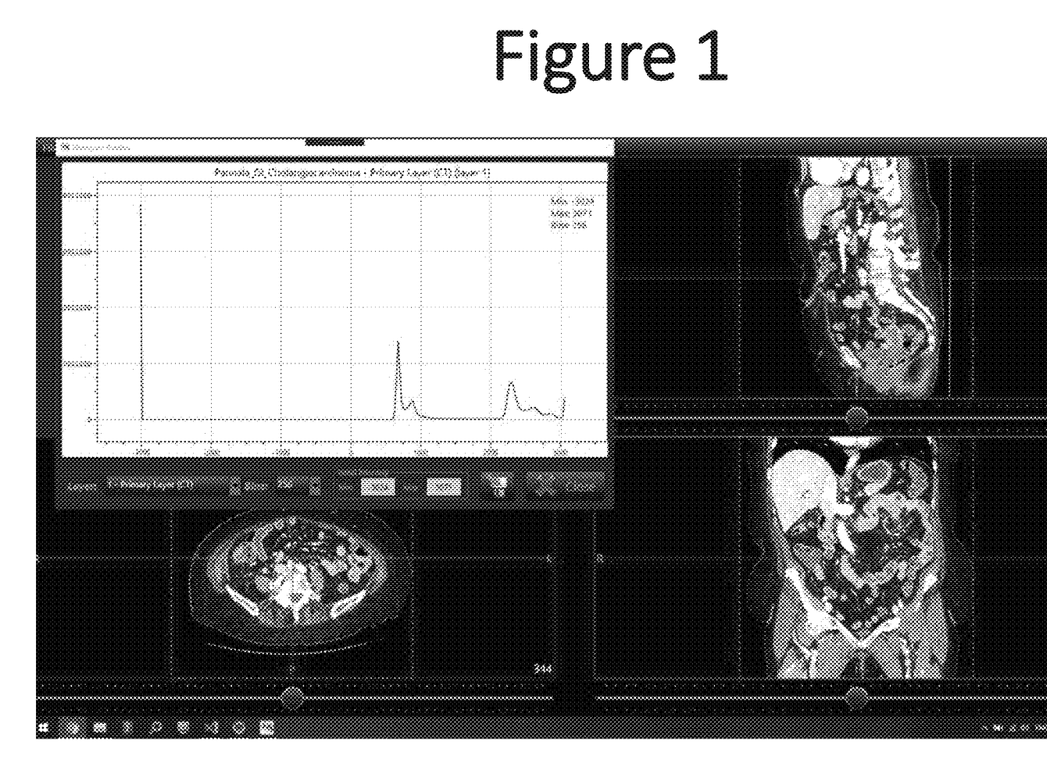
FIG. 1 illustrates an example histogram of the images shown in the figure.
Figure 5:
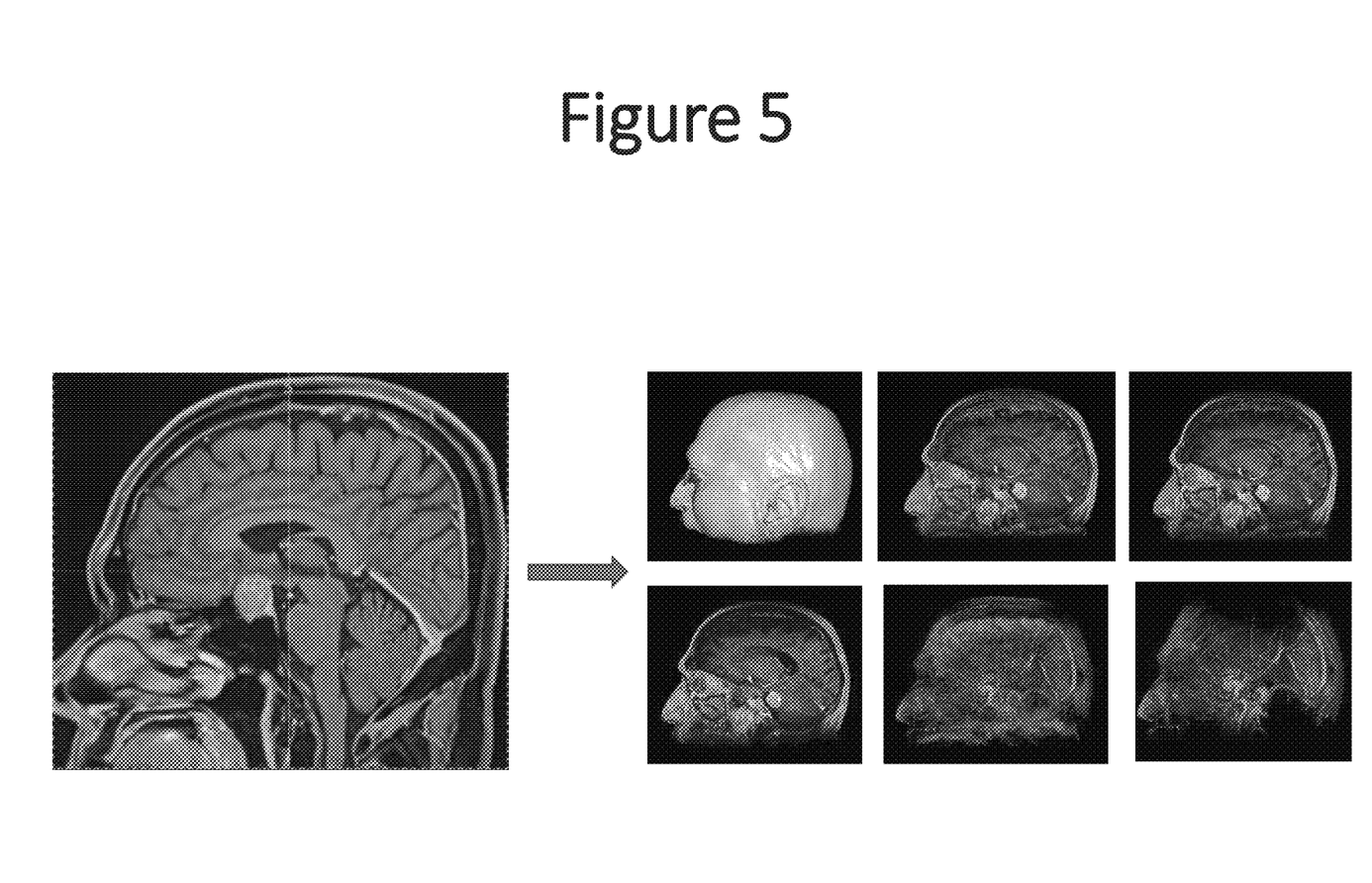
FIGS. 5-6 illustrate examples of transfer function features.
Figure 6:
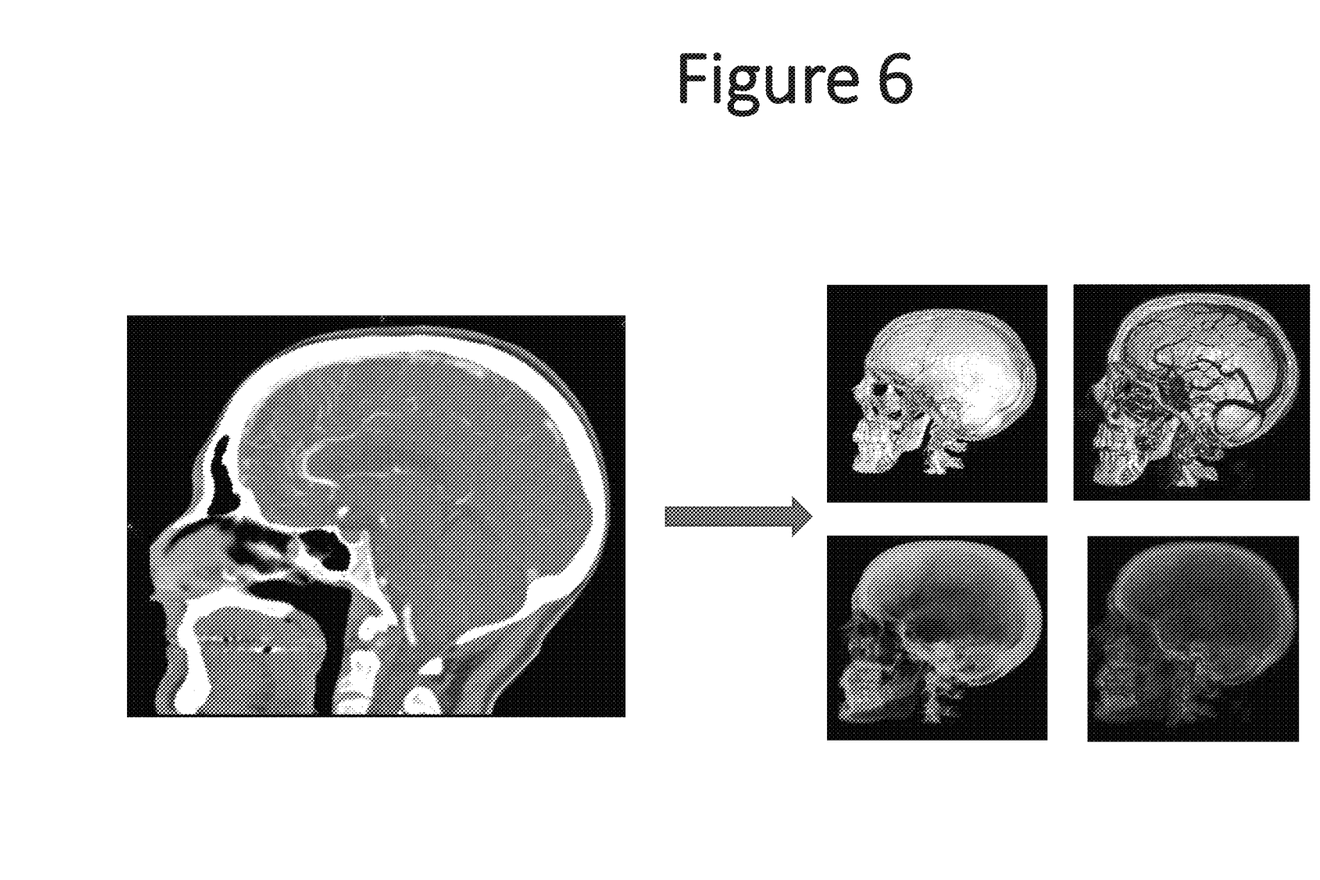
Figure 7:
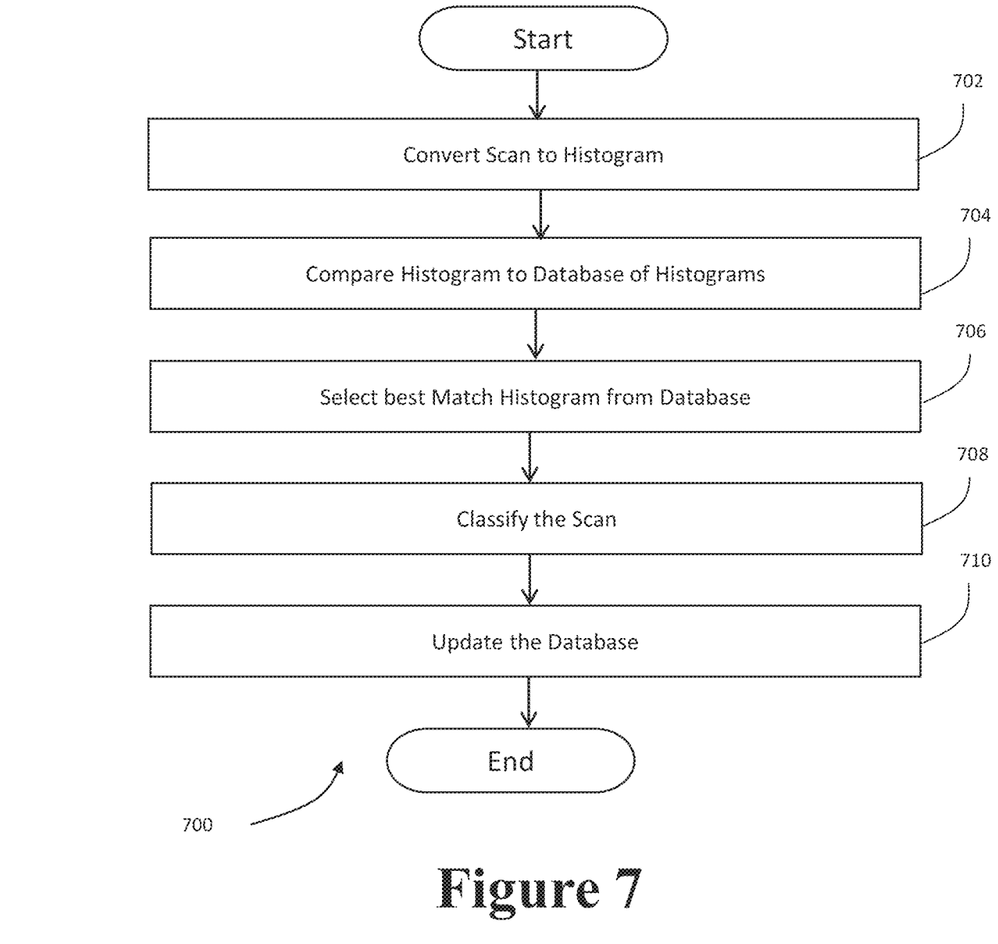
FIG. 7 provides a flow chart of one example histogram matching process to automatically determine a transfer function.

FIG. 7 provides an example process for automatically finding an appropriate transfer function for a given new model through use of histograms, such as shown in the example of FIG. 1. FIGS. 2-6 describe, in more detail, an example system for automating a transfer function. A transfer function, for example, may be a setting in a surgery rehearsal and preparation tool or another suitable medical imaging tool that provides a typical view. For example, When a DICOM scan is received, it is made up of many voxels (similar to pixels for regular images). Different anatomy shows up at different intensity values in DICOM and different intensities also means they show up at different brightness levels. For example, in a contrast CTA the bone is high intensity followed by contrast filled blood vessels. A transfer function assigns a color and an opacity for a range of voxels. For example if all of the voxels that are showing bone appear at range of intensity levels between 4000 and 5000, this range may be assigned to be white for bone, and if is desirable for the bone to be solid the opacity could be set to 100%. This combination of voxel intensity range and opacity is a setting that enables visualization of the bone in a 3D model and is an example of a transfer function. This can be done for different scans showing different pieces of anatomy.

The automatic transfer function determining system described herein automatically analyzes the voxel intensities frequency and distribution of a current volumetric DICOM scan. These intensities are analyzed as a histogram. The software compares this histogram to a library of verified histograms from previous cases and scan modality. Anonymity of patient personal information is maintained during this process. These previous cases have had transfer functions created for them, perhaps manually using skilled and experienced personnel, that correlate to their histogram and display different anatomical components. The system manipulates (stretches/shrinks) the histogram and associated transfer function of the new scan with that of the case from a library that is most similar by stretching, shrinking, and translating the automatic transfer function graph to coincide with histogram peaks, to facilitate the matching process described herein.

To aid the described system, a database of transfer functions associated with historical cases or scans may be compiled by reviewing the historical cases and ensuring or approving the quality of the associated transfer functions, some of which may have been manually created and verified for accuracy. This results in a collection of cases and transfer functions with high quality segmentation for a variety of different types of models based on a variety of patients. This database of historical transfer functions is then used by the system to automatically suggest a transfer function for a future case that would result in an ideal or desirable 3D model.

It should be appreciated that a histogram, as that term is used herein, is based on the one or more scans of particular anatomical features of a specific patient, resulting in a signature of the scan(s) of the particular anatomical feature of the specific patient, and will be the same for a typical scan of the anatomical feature regardless of the patient from which the scan is taken. Hence, the histogram is closely associated with the particular anatomical features being scanned, and to be modeled. Accordingly, using artificial intelligence and algorithms described herein, the system uses the histogram as a basis for automatically suggesting a potential transfer function for a new case or scan by comparing the histogram of the new scan to the plurality of verified histograms of previous scans of the particular anatomical features provided in the historical database. The system assigns a grade to histograms based on the comparison which represents the closeness of the match (e.g., higher scores represent better matches) and then assigns a transfer function associated with the histogram having the best grade. A threshold value for the score may be determined in advance to ensure that the match is sufficiently close to provide accurate results, such that if no sufficiently close match (i.e., meeting or surpassing the threshold) is found, then a new transfer function will be prepared for the new scans.

The database of histograms is provided with a transfer function (or plurality of transfer functions providing different features) associated with each respective histogram. These can each be categorized by particular anatomical features being scanned, (and in the situation where different types of transfer functions are provided, by type of transfer function), and such categorization might be further broken into other useful categories or tags that might aid the matching effort, such as the type of scan, the equipment used for the scan, specific features about the patient or the particular anatomical features, the orientation of the patient during the scan, etc. Matching can then be improved by utilizing the categories or tags to better ensure effective matches. An artificial intelligence program can be utilized to perform the matching, and such a program can be designed to learn from the matching process to improve the matching effectiveness over time.

The AI program will utilize features of the histograms, such as overall shape, intensities (e.g., peaks and valleys), patterns, etc. that are effective in ensuring accurate selection of transfer functions. A learning AI program can learn from its mistakes and its successes, requiring less and less manual oversight over time.

FIG. 7 broadly illustrates an example method for automatic transfer function, with FIGS. 2-6 providing more detailed examples, as described below.

Figure 2:
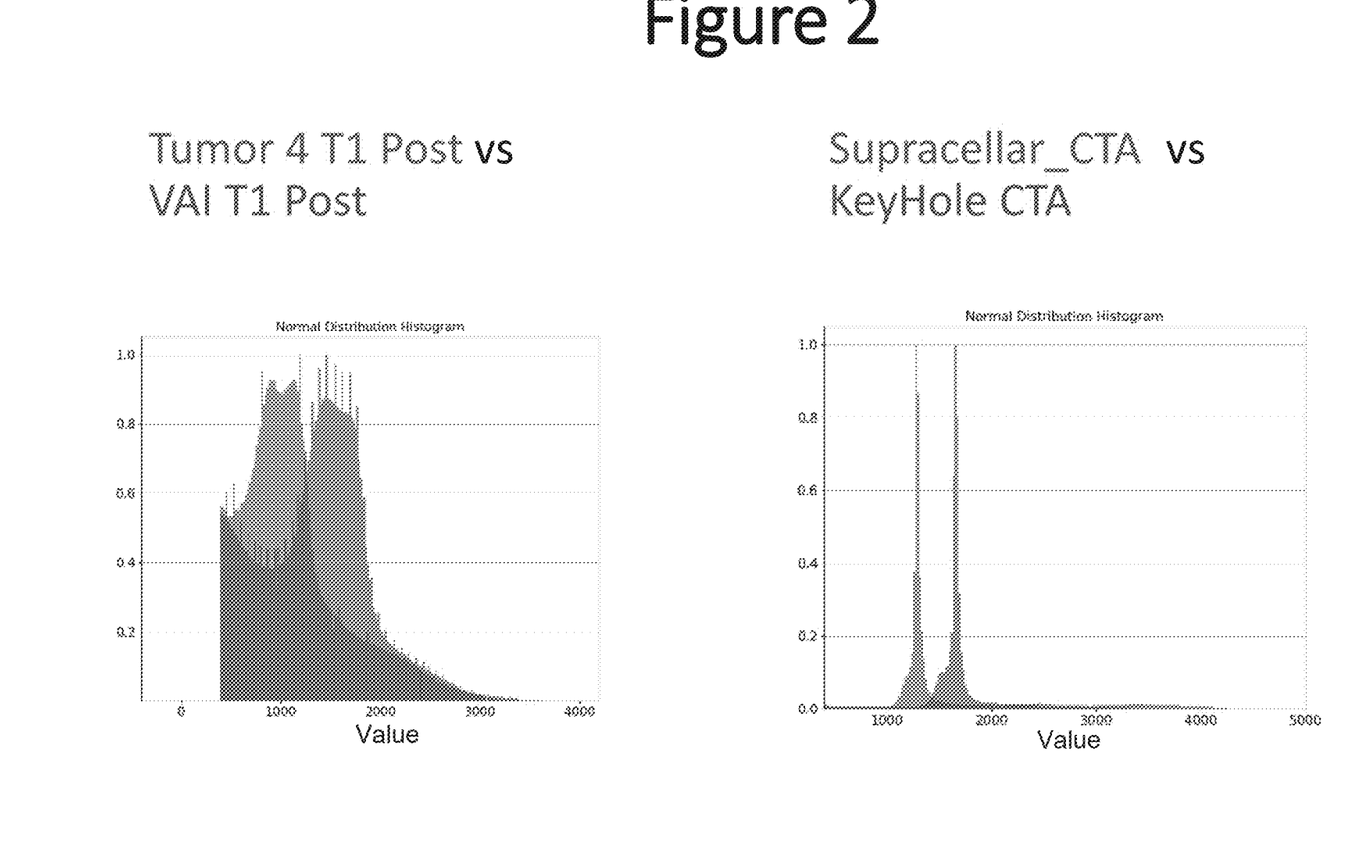
FIG. 2 illustrates additional example histograms that have been scaled.

At block 702 of FIG. 7, a scan is received and converted to a current histogram of a feature of interest, such as voxel intensities. FIG. 2 shows two examples of such histograms, in this case normal distribution histograms (other types of distributions could be alternatively utilized, or use together to better ensure a good match). The histograms of FIG. 2 have been rescaled (0-5000) with values 0-200 being clipped out. Note that the transfer function from one scan will not fit the other scan without adjustments.

Figure 3:
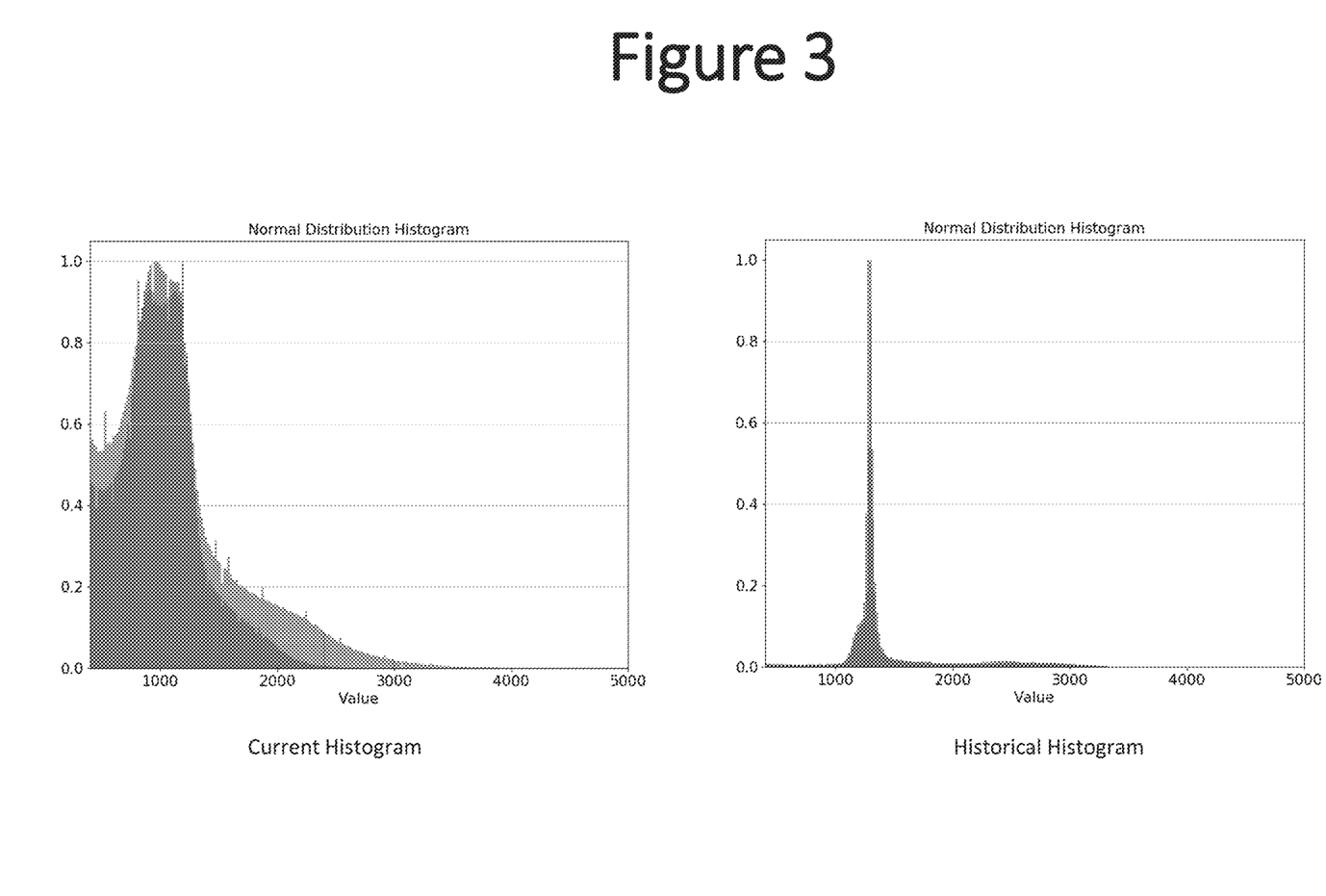
FIG. 3 illustrates an example comparison between a current histogram and a historical histogram.
Figure 4:
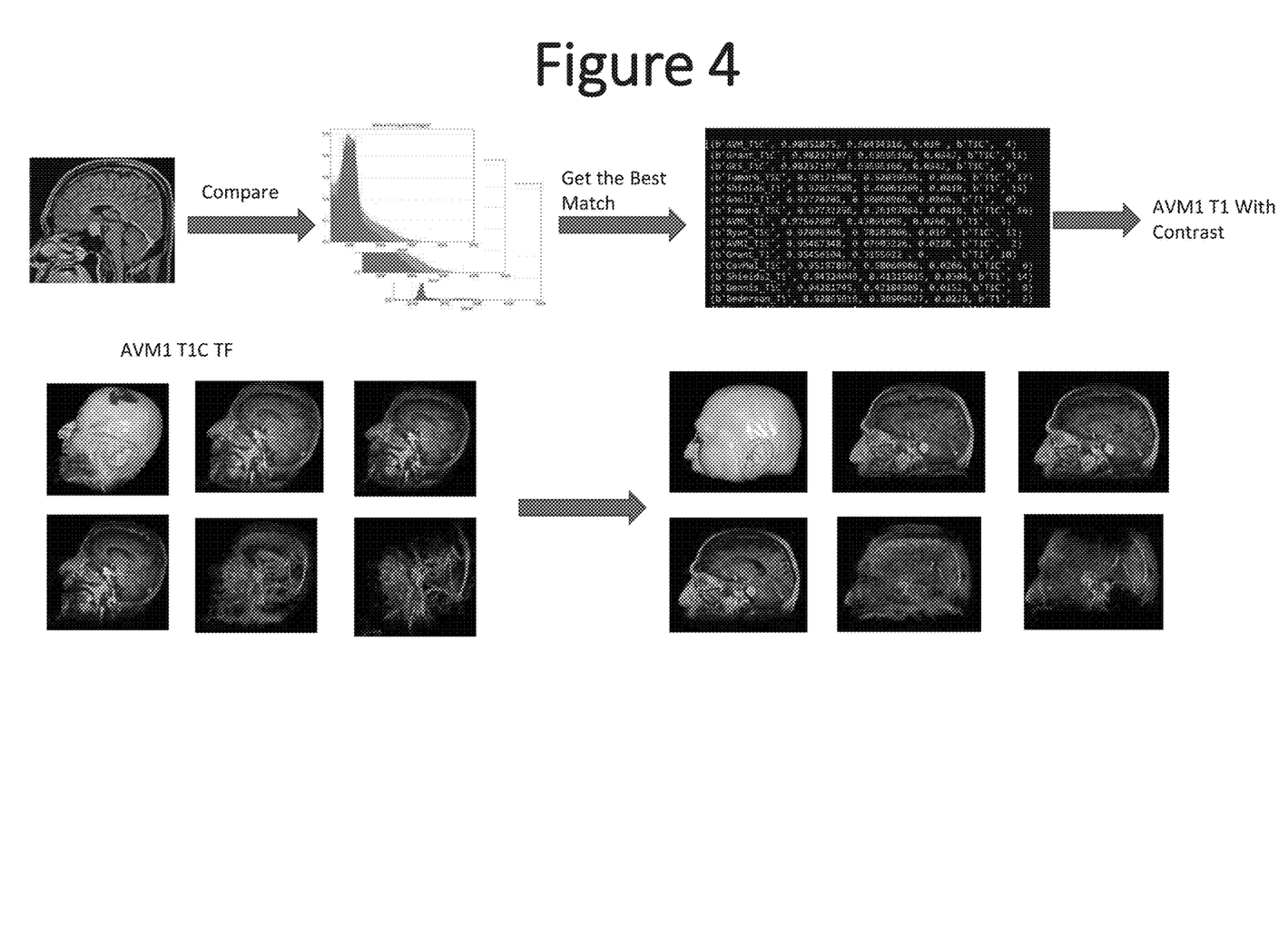
FIG. 4 illustrates an example histogram comparison process for automatically determining a transfer function.

At 704 of FIG. 7, the current histogram is compared with other historical histograms provided in a database to find the best match (typically after processing the histogram created). FIG. 3 shows an example of current and historical histograms, and FIG. 4 shows an example of such a matching process for matching a current histogram representing a new scan to a historical histogram representing a previously performed scan. The example matching process comprises steps (1) find the max histogram bin on both scans; (2) rescale the current histogram to match max bin for both scans; (3) close range search by shifting, such as shifting the current histogram left and right to improve match results; and (4) score the match results. The match scoring provides a score between 0 and 1 that represents the closeness of the match, with 0 representing no match and a 1 representing a perfect, or nearly perfect, match. These scores can be based on criteria determined by initially manually performing the process, and mathematically providing a scoring algorithm that can be automatically applied.

As discussed above, the current histogram may be manipulated to better support the matching function, such as by expanding, compressing, colorizing, etc. the histogram prior to comparing with the historical histograms. The shifting process in the example step is on such option. This can put the current histogram into a more standardized format for performing the comparison.

This process is then repeated by comparing the current histogram to a plurality of historical histograms until a sufficient match is found (such as when a score match threshold is met, or the highest score determined). FIG. 4 shows this process graphically.

At 706 in FIG. 7, based on the processing of the histogram and the matching process, a transfer function from the identified best match histogram, if one is found, is selected, and a new transfer function is created based on the selected transfer function for the new scan. This new transfer function might be modified to better satisfy the needs of the current model, or the historical transfer function might be used as-is. FIGS. 5 and 6 show examples of this process graphically. FIG. 5 shows transfer features including: face, greyscale tissue vents vessels, tissue vents vessels, tissue vessels, vents vessels, and other vessels. FIG. 6 shows transfer features including: bone, bone vessels, transparent bone, and transparent bone vessels.

At 708 in FIG. 7, in one example the scan is classified as a subclass of a modality (for example CT modality can have sub-modalities of CT or CTA). At 710, the system is further trained by adding new scan based histograms to the database associated with the new transfer function in order to improve the artificial intelligence algorithm of the system, thus improving the algorithm's ability to find better matches to new scans. Adding new histograms to the database can be done in cases where the result was not satisfactory (e.g., a match threshold was not met), or the classification was wrong, such that a new transfer function is prepared from scratch to represent the new scan and its histogram, or where the transfer function obtained from the match has been modified to make it more accurate. Adding the scan, histogram, and new transfer function to the database with the correct classification improves the system's accuracy and ability to classify and match histograms.

Figure 8:
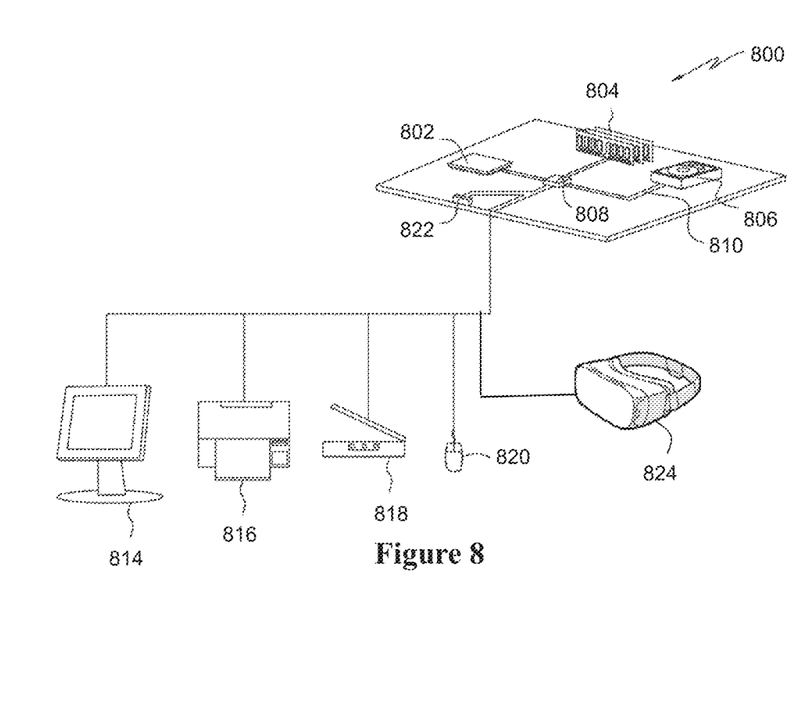
FIG. 8 is a block diagram of an example computer for implementing an example automatic transfer function system of FIGS. 1-7.

FIG. 8 is a schematic diagram of an example computer 800 for implementing the example automatic transfer function system described in FIGS. 1-7. The example computer 800 is intended to represent various forms of digital computers, including laptops, desktops, handheld computers, tablet computers, smartphones, servers, and other similar types of computing devices. Computer 800 includes a processor 802, memory 804, a storage device 806, and a communication port 808, operably connected by an bus 810 via an interface 822. Processor 802 processes instructions, via memory 804, for execution within computer 800. In an example embodiment, multiple processors along with multiple memories may be used.

Memory 804 may be volatile memory or non-volatile memory. Memory 804 may be a computer-readable medium, such as a magnetic disk or optical disk. Storage device 806 may be a computer-readable medium, such as floppy disk devices, a hard disk device, optical disk device, a tape device, a flash memory, phase change memory, or other similar solid state memory device, or an array of devices, including devices in a storage area network of other configurations. A computer program product can be tangibly embodied in a computer readable medium such as memory 804 or storage device 806.

Computer 800 can be coupled to one or more input and output devices such as a display 814, a printer 816, a scanner 818, a mouse 820, and an HMD 824.

As will be appreciated by one of skill in the art, the example embodiments may be actualized as, or may generally utilize, a method, system, computer program product, or a combination of the foregoing. Accordingly, any of the embodiments may take the form of specialized software comprising executable instructions stored in a storage device for execution on computer hardware, where the software can be stored on a computer-usable storage medium having computer-usable program code embodied in the medium.

Databases may be implemented using commercially available computer applications, such as open source solutions such as MySQL, or closed solutions like Microsoft SQL that may operate on the disclosed servers or on additional computer servers. Databases may utilize relational or object oriented paradigms for storing data, models, and model parameters that are used for the example embodiments disclosed above. Such databases may be customized using known database programming techniques for specialized applicability as disclosed herein.

Any suitable computer usable (computer readable) medium may be utilized for storing the software comprising the executable instructions. The computer usable or computer readable medium may be, for example but not limited to, an electronic, magnetic, optical, electromagnetic, infrared, or semiconductor system, apparatus, device, or propagation medium. More specific examples (a non-exhaustive list) of the computer readable medium would include the following: an electrical connection having one or more wires; a tangible medium such as a portable computer diskette, a hard disk, a random access memory (RAM), a read-only memory (ROM), an erasable programmable read-only memory (EPROM or Flash memory), a compact disc read-only memory (CDROM), or other tangible optical or magnetic storage device; or transmission media such as those supporting the Internet or an intranet.

In the context of this document, a computer usable or computer readable medium may be any medium that can contain, store, communicate, propagate, or transport the program instructions for use by, or in connection with, the instruction execution system, platform, apparatus, or device, which can include any suitable computer (or computer system) including one or more programmable or dedicated processor/controller(s). The computer usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, local communication busses, radio frequency (RF) or other means.

Computer program code having executable instructions for carrying out operations of the example embodiments may be written by conventional means using any computer language, including but not limited to, an interpreted or event driven language such as BASIC, Lisp, VBA, or VBScript, or a GUI embodiment such as visual basic, a compiled programming language such as FORTRAN, COBOL, or Pascal, an object oriented, scripted or unscripted programming language such as Java, JavaScript, Perl, Smalltalk, C++, Object Pascal, or the like, artificial intelligence languages such as Prolog, a real-time embedded language such as Ada, or even more direct or simplified programming using ladder logic, an Assembler language, or directly programming using an appropriate machine language.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

While the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the application, in its broader aspects, is not limited to the specific details, the representative apparatus and method, and illustrative examples shown and described. Accordingly, departures may be made from such details without departing from the spirit or scope of the applicant's general inventive concept.

What is claimed is:

1. A method for using a computer system to automatically determine a transfer function for use with a 3D model, comprising the steps of:
    storing a plurality of histograms in a database, each one of said histograms derived from one or more associated medical scans of a particular anatomical feature of a respective one of a plurality of different patients;
    storing a plurality of transfer functions in the database, each one of said transfer functions being associated with a respective one of said plurality of histograms;
    generating a current histogram from a specific medical scan of the particular anatomical feature of a particular patient using the computer system;
    the computer system automatically comparing the current histogram to each one of said plurality of histograms to determine if one of said plurality of histograms is sufficiently similar to the current histogram;
    if it was determined that one of said plurality of histograms is sufficiently similar to the current histogram, select the transfer function associated with the one of said plurality of histograms for preparing a model of the particular anatomical feature; and
    if it was determined that none of said plurality of histograms was sufficiently similar to the current histogram, generate a new transfer function for preparing a 3D model of the particular anatomical feature.

2. The method of claim 1, further comprising the steps of, if it was determined that none of said plurality of histograms was sufficiently similar to the current histogram:
    adding the current histogram to the plurality of histograms stored in the database; and adding the new transfer function to the plurality of transfer functions stored in the database, said new transfer function being associated with the current histogram.

3. The method of claim 1, where said step of automatically comparing the current histogram to each one of said plurality of histograms includes the steps of: adjusting the current histogram into a desired format; and comparing the current histogram, as adjusted, to each one of said plurality of histograms to determine if one of said plurality of histograms is sufficiently similar to the current histogram.

4. The method of claim 1, wherein said histograms are each configured to capture voxel intensity values of the associated medical scan.

5. The method of claim 4, wherein said transfer functions are each configured to map the voxel intensity values to color and opacity.

6. The method of claim 5, wherein the model, using the new or selected transfer function, provides the ability to control tissue intensity of the particular anatomical feature to enable a user to see features that would otherwise not be seen when using a model.

7. The method of claim 6, wherein the ability to control tissue intensity permits users to see behind biological structures that would otherwise block such a view.

8. The method of claim 1, where said step of automatically comparing the current histogram to each one of said plurality of histograms includes the steps of:
for each one of said plurality of histograms, comparing the current histogram to the one of said plurality of histograms to assign a score indicating similarity between the current histogram and the one of the histograms; and
determining that the one of said plurality of histograms having the score with the highest value is sufficiently similar to the current histogram.

9. The method of claim 1, where said step of automatically comparing the current histogram to each one of said plurality of histograms includes the steps of:
for each one of said plurality of histograms, comparing the current histogram to the one of said plurality of histograms to assign a score indicating similarity between the current histogram and the one of the histograms; and
determining that the one of said plurality of histograms with the score having the score with the highest value is sufficiently similar to the current histogram if the score having the highest value exceeds a threshold value.

10. A system including the computer system and the database for performing the method of claim 1.

11. A method for using a computer system to automatically determine a transfer function for use with a 3D model, comprising the steps of:
storing a plurality of histograms in a database, each one of said histograms derived from one or more associated image scans of a particular feature of a respective one of a plurality of different subjects;
storing a plurality of transfer functions in the database, each one of said transfer functions being associated with a respective one of said plurality of histograms;
generating a current histogram from an image scan of the particular feature of a particular subject using the computer system;
for each one of the plurality of histograms, the computer system automatically comparing the current histogram to the one of said plurality of histograms to assign a score indicating similarity between the current histogram and the one of the histograms;
determine whether the score having the highest value is above a threshold value to indicate that the current histogram is sufficiently similar to the one of the plurality of histograms associated with said score with the highest value;
if it was determined that one of said plurality of histograms associated with the highest score is sufficiently similar to the current histogram, select the transfer function associated with the one of said plurality of histograms associated with the highest score for preparing a 3D model of the particular feature;
if it was determined that none of said plurality of histograms was sufficiently similar to the current histogram, generate a new transfer function for preparing a 3D model of the particular feature;
adding the current histogram to the plurality of histograms stored in the database; and
adding the new transfer function to the plurality of transfer functions stored in the database, said new transfer function being associated with the current histogram.

12. The method of claim 11, where said step of automatically comparing the current histogram to each one of said plurality of histograms includes the steps of: adjusting the current histogram into a desired format; and comparing the current histogram, as adjusted, to each one of said plurality of histograms to determine if one of said plurality of histograms is sufficiently similar to the current histogram.

13. The method of claim 11, wherein said histograms are each configured to capture voxel intensity values of an image scan.

14. The method of claim 13, wherein said transfer functions are each configured to map the voxel intensity values to color and opacity.

15. The method of claim 14, wherein the 3D model, using the selected or new transfer function, provides the ability to control image intensity of the particular feature to enable a user to see features that would otherwise not be seen when using a model.

16. The method of claim 15, wherein the ability to control image intensity permits users to see behind structures in the 3D that would otherwise block such a view.

17. A system including the computer system and the database for performing the method of claim 11.

18. A method for using a computer system to automatically determine a transfer function for use with a 3D model, comprising the steps of:
storing a plurality of histograms in a database, each one of said histograms derived from one or more associated medical scans of a particular biological feature of a respective one of a plurality of different patients;
storing a plurality of transfer functions in the database, each one of said transfer functions being associated with a respective one of said plurality of histograms;
generating a current histogram from an image scan of the particular biological feature of a particular patient using the computer system;
for each one of the plurality of histograms, the computer system automatically comparing the current histogram to the one of said plurality of histograms to assign a score indicating similarity between the current histogram and the one of the histograms;
determine whether the score having the highest value is above a threshold value to indicate that the current histogram is sufficiently similar to the one of the plurality of histograms associated with said score with the highest value;

if it was determined that one of said plurality of histograms associated with the highest score is sufficiently similar to the current histogram, select the transfer function associated with the one of said plurality of histograms associated with the highest score for preparing a 3D biological model of the particular biological feature;

if it was determined that none of said plurality of histograms was sufficiently similar to the current histogram, generate a new transfer function for preparing a 3D biological model of the particular feature;

adding the current histogram to the plurality of histograms stored in the database; and adding the new transfer function to the plurality of transfer functions stored in the database, said new transfer function being associated with the current histogram.

19. The method of claim 18, wherein said histograms are each configured to capture voxel intensity values of the associated medical scan.

20. The method of claim 19, wherein said transfer functions are each configured to map the voxel intensity values to color and opacity.

21. The method of claim 20, wherein the 3D model, using the selected or new transfer function, provides the ability to control tissue intensity of the particular anatomical feature to enable a user to see features that would otherwise not be seen when using the model.

22. The method of claim 21, wherein the ability to control tissue intensity permits users to see behind biological structures that would otherwise block such a view.

23. A system including the computer system and the database for performing the method of claim 18.

24. A method for using a computer system to automatically determine a transfer function for use with a 3D model, comprising the steps of:

storing a plurality of histograms in a database, each one of said histograms capturing voxel intensity values from one or more associated medical scans of a particular biological feature of a respective one of a plurality of different patients;

storing a plurality of transfer functions in the database, each one of said transfer functions being associated with a respective one of said plurality of histograms and being configured to map the voxel intensity values to color and opacity;

generating a current histogram from an image scan of the particular biological feature of a particular patient using the computer system;

for each one of the plurality of histograms, the computer system automatically comparing the current histogram to the one of said plurality of histograms to assign a score indicating similarity between the current histogram and the one of the histograms;

determine whether the score having the highest value is above a threshold value to indicate that the current histogram is sufficiently similar to the one of the plurality of histograms associated with said score with the highest value;

if it was determined that one of said plurality of histograms associated with the highest score is sufficiently similar to the current histogram, select the transfer function associated with the one of said plurality of histograms associated with the highest score for preparing a 3D biological model of the particular biological feature;

if it was determined that none of said plurality of histograms was sufficiently similar to the current histogram, generate a new transfer function for preparing a 3D biological model of the particular feature;

adding the current histogram to the plurality of histograms stored in the database; and adding the new transfer function to the plurality of transfer functions stored in the database, said new transfer function being associated with the current histogram, wherein the 3D biological model, using the selected or new transfer function, provides the ability to control tissue intensity of the particular anatomical feature to enable a user to see features that would otherwise not be seen when using the model.

25. The method of claim 24, wherein the ability to control tissue intensity permits users to better see certain biological structures in the 3D model.

26. A system including the computer system and the database for performing the method of claim 24.

* * * * *